United States Patent [19]

Bohn et al.

[11] 4,269,825

[45] May 26, 1981

[54] NEW GLYCOPROTEIN AND PROCESS FOR ISOLATING IT

[75] Inventors: Hans Bohn, Marburg; Wilhelm Winckler, Wenkbach, both of Fed. Rep. of Germany

[73] Assignee: Behringwerke AG, Marburg, Fed. Rep. of Germany

[21] Appl. No.: 105,416

[22] Filed: Dec. 19, 1979

Related U.S. Application Data

[63] Continuation of Ser. No. 915,261, Jun. 13, 1978, abandoned.

[30] Foreign Application Priority Data

Jun. 15, 1977 [DE]  Fed. Rep. of Germany ....... 2726886

[51] Int. Cl.$^3$ .................. A61K 39/00; C07G 7/00
[52] U.S. Cl. ................. 424/85; 260/112 R; 260/112 B; 424/101
[58] Field of Search .............. 260/112 R, 112 B; 424/85, 88, 101

[56] References Cited

PUBLICATIONS

Bohn, H., Protides Biol. Fluids, 24, pp. 117–124, (1976).

Bohn, H., Arch. Gynaekol, vol. 212, pp. 165–175, (1972).
Bohn, H., Blut, vol. 24, pp. 292–302, (1972).
Bohn, H., Arch. Gynaekol, vol. 221, pp. 73–81, (1976).
Bohn, H., Arch. Gynaekol, vol. 218, pp. 131–142, (1975).

*Primary Examiner*—Delbert R. Phillips
*Assistant Examiner*—Blondel Hazel
*Attorney, Agent, or Firm*—Curtis, Morris & Safford

[57] ABSTRACT

A new glycoprotein is characterized by a protein consisting essentially of 75±6% of α-amino-acids, a carbohydrate portion of 24.6±5.2%, which contains 8.9±2% of hexoses, 7.1±1.5 of N-acetylated hexosamine, 0.2±0.2% of fucose, 8.4±1.5% of, N-acetylated neuraminic acid; a sedimentation coefficient $S_{20w}$ of 2.5±0.3 S; a molecular weight of 35,000±5,000, determined in the ultracentrifuge, and a molecular weight of 65,000±10,000, determined in polyacrylamide gel containing sodium dodecyl sulfate; an iso-electric point at pH 3.4±0.4; an extinction coefficient $E_1\%_{cm}$ (280 nm) of 1.9±0.3; an electrophoretic mobility in the range between that of $\alpha_1$ and $\alpha_2$-globulins; and a specific immunologic reaction with an antibody specifically directed against the glycoprotein.

3 Claims, No Drawings

NEW GLYCOPROTEIN AND PROCESS FOR ISOLATING IT

This is a continuation, of application Ser. No. 915,261, filed June 13, 1978 now abandoned.

The present invention relates to a new glycoprotein which can be found in the blood serum and in extracts of human placentas and which can be isolated therefrom, as well as to a process for isolating it.

It is known that the protein solution obtained by aqueous extraction of human placentas contains a great number of components, which are partly serum proteins and partly tissue proteins.

The task set for the present invention was to isolate a hitherto unknown glycoprotein from an extract of human placentas, to prepare with it antiserums which are specifically directed against the new glycoprotein and permit proving the presence of the new glycoprotein in the serum qualitatively or determining it quantitatively.

Thus, the object of the invention is a new glycoprotein which can be isolated from the blood serum and the extract of human placentas. It is characterized by:

A protein portion essentially consisting of 75±6% of α-amino-acids, a carbohydrate portion of 24.6±5.2%, which contains 8.9±2% of hexoses, 7.1±1.5 of N-acetylated hexosamine, 0.2±0.2% of fucose, and 8.4±1.5% of N-acetylated neuraminic acid;

a sedimentation coefficient $S_{20w}$ of 2.5±0.3 S;

a molecular weight of 35,000±5,000, determined in the ultracentrifuge, and a molecular weight of 65,000±10,000, determined in polyacrylamide gel containing sodium dodecyl sulfate;

an iso-electric point at pH 3.4±0.4;

an extinction coefficient $E_{1\,cm}^{1\%}$ (280 nm) of 1.9±0.3;

an electrophoretic mobility in the range between that of $\alpha_1$ and $\alpha_2$-globulins; and a specific immunologic reaction with an antibody specifically directed against the glycoprotein.

The following explanations are given in order to clarify the characteristics of the glycoprotein:

Determination of the sedimentation coefficient was effected in an analytical ultra-centrifuge of Messrs. Beckmann (Spinco-Apparatus, type E), at 6,000 rev./m. in double sector cells with the aid of ultraviolet scanner technique at 280 nm. The solvent was a 0.05 M phosphate buffer (pH 6.8) which contained 0.2 mol/l of NaCl. The protein concentration was 2%. The sedimentation coefficients were calculated on the basis of water at 20° C.

In order to determine the molecular weight, the method of equilibrium of sedimentation and electrophoresis in polyacrylamide gel were used. Determination in the ultracentrifuge was carried out at 9,000 rev./min. The evaluation was made on the basis of a partial specific volume of 0.74 ml/g. In the ultracentrifuge, a molecular weight of 35,000±5,000 was found.

For the electrophoresis in polyacrylamide gel, two methods were used. A separation in normal polyacrylamide (PAA)-gel was carried out according to the method of Zwisler and Biel, Z.klin.Chem. 4, page 58 (1966). For the test in a gel containing sodium dodecyl sulfate, a gel containing 7.5% of PAA and 0.1% of sodium dodecyl sulfate (SDS) was used. For reduction, the proteins were incubated in SDS with 1% mercaptoethanol. The proteins were dyed with amido black. The migration within the SDS-containing PAA-gel indicated a molecular weight of 65,000±10,000 for the glycoprotein.

The determination of the iso-electric point was effected with a column (440 ml) of Messrs. LKB Stockholm. The so-called Ampholine mixture used had a pH-value of from 3 to 5.

The test for the electrophoretic mobility was effected according to the micro-modification of Beckmann Instruments on cellulose acetate foils with a sodium diethyl barbiturate buffer of pH 8.6.

Determination of the carbohydrates was carried out according to the method described by H. E. Schultze, R. Schmidtberger, H. Haupt, Biochem. Z, 329, page 490 (1958).

The analysis for amino-acids was carried out according to S. Moore, D. H. Spackmann, W. H. Stein, Anal.-Chem. 30, page 1185, (1958), using the liquid chromatograph Multichrom B of Messrs. Beckmann. ½ Cystine was determined after oxidation of the proteins with per-formic acid [S. Moore et al., Anal. Chem. 30, page 1185, (1958)] and subsequent chromatography [S. Moore, J.Biol.Chem. 238, page 235, (1963)] as cysteinic acid. The content of tryptophan was determined by direct photomeric measurement according to H. Edelhoch, Biochemistry 6, page 1948, (1967).

The immunologic characterization of the substance was effected in the most simple way according to a known diffusion process in which the antigen, i.e. the glycoprotein, and an antibody directed against the glycoprotein or antiserum which is not enriched with regard to antibodies, are allowed to diffuse against each other in a carrier medium, for example agar-agar. If both reaction components meet in a favorable proportion, a visible precipitate is formed. With this knowledge, it is obvious to an expert that all immunological techniques for the detection and determination of the new glycoprotein as well as of the antibodies directed against this glycoprotein are possible.

A simple and generally sufficiently exact method for the quantitative determination of the glycoprotein in body liquids or in tissue extracts is the so-called Laurell-technique. It is described in Analyt. Biochem. (New York), 15, page 45 (1966).

The present invention furthermore provides a process for isolating the above specified glycoprotein, which comprises fractionating body liquids or extracts of organs which contain the glycoprotein, on the basis of the criteria found according to the invention.

The glycoprotein can be precipitated with neutral salts. With ammonium sulfate, which is usually employed for such precipitations, the glycoprotein is precipitated at a saturation concentration of the salt of from 30 to 60% in a pH-range in proximity of the neutral point.

According to its molecular weight, the glycoprotein can be isolated by measures which are suitable for the separation of substances with molecular weights between 25,000 and 75,000. It is of advantage to use the methods of gel-filtration or ultra-filtration for this purpose.

The glycoprotein is adsorbed on weakly basic ionexchangers at a neutral or weakly alkaline pH-value. It is of advantage to use a buffer solution which has a relatively low concentration, because by increasing the salt concentration or by lowering the pH-value the adsorption can be prevented. On the other hand, when knowing this behaviour, the possibility is presented of adsorbing the glycoprotein and then eluting it again by using more highly concentrated salt solutions or buffer solutions with reduced pH-value.

It has been found that the new glycoprotein is not precipitated by the water-soluble organic bases of the acridine and quinoline series which are normally used for protein precipitation methods. At the concentrations usually employed in these processes, it remains in the aqueous supernatant. Accordingly, an acridine base, such as 2-ethoxy-6,9-diamino-acridine lactate or a quinoline base such as bis-(2-methyl-4-aminoquinolyl-6)-carbamide hydrochloride, can be used for the precipitation of accompanying proteins, the glycoprotein of the invention remaining in the supernatant.

The considerations are similar with the use of hydroxyl-apatite as an adsorbant for proteins. The new glycoprotein shows no affinity for hydroxyl-apatite, whereas a series of accompanying proteins are adsorbed on hydroxyl-apatite. Thus, the glycoprotein belongs to the globulins passing through hydroxyl-apatite so that the inventors propose to designate the glycoprotein as a hydroxyl-apatite-passing globulin (HPG-2).

On the basis of the knowledge of the electrophoretic mobility, preparative zone electrophoresis can be used for the enrichment or isolation of the glycoprotein.

The affinity of the glycoprotein due to its immunological behavior may be used to enrich the glycoprotein with the aid of so-called immuno-adsorption processes. For the purpose, an immuno-adsorbant, i.e., a carrier-bound antibody directed against the new glycoprotein and which is capable of specifically binding the glycoprotein, can be prepared in known manner. The glycoprotein can subsequently be eluted again by modification of the conditions of the medium as described in the relevant literature.

Isolation of the substance of the present invention can thus be effected by a selected combination of the above-mentioned methods which lead, on the one hand, to an enrichment of the glycoprotein, and, on the other hand, to its separation from other accompanying proteins. Accordingly, the subject of the present invention resides in the individual steps for enriching the new glycoprotein and in the processes for its purification reached by a combination of these measures. The guideline for the process for preparing the glycoprotein consists in isolating in each case that portion which shows a positive immunological reaction with an antiserum directed against the new glycoprotein.

After having carried out the above-described process steps, it has been found in some cases that the glycoprotein is still contaminated by other accompanying proteins which are immunologically detectable. In this case, the contaminating substances are eliminated by their specific adsorption. For this purpose the common methods of immuno-adsorption are used, according to which antibodies bound to a carrier and directed against the protein to be eliminated are employed as adsorbants. In many cases, the substantially pure new glycoprotein still contains traces of pregnancy-specific $\beta_1$-glycoprotein and/or $\alpha_1$-B-glycoprotein, which is also designated as easily-precipitable $\alpha_1$-glycoprotein. For their separation, immunoglobulins which are directed against the proteins and which are bound covalently on cross-linked agar preparations, for example those available under the trade name "Sepharose", are used.

The protein solution introduced into a column filled with the specific immuno-adsorbant passes throught the column without hindrance, since only those components are bound against which the carrier contains an immunological active partner. In this manner the new glycoprotein can be freed from impurities.

For preparing the new glycoprotein, several of the measures indicated above are combined with one another and in each step only that fraction is further treated in which the new glycoprotein can be proved immunologically, whereas the remaining fractions are rejected.

As starting material for the isolation of the new glycoprotein, any body fluid or every organ extract may be used in which the glycoprotein can be proved immunologically. It is preferred to use extracts of human placentas which are obtained by comminution and extraction with water or dilute, suitably less than 10%, salt solution, advantageously 0.5% salt solution, for example sodium chloride. Suitably, about 1–5 liters of extraction solution are used for 1 kg of placentas. Undissolved matter is separated from the extract by centrifugation or filtration.

The enrichment process is characterized in that at least one of the following process steps is applied to body fluids containing the new glycoprotein and the fraction with the enriched glycoprotein is isolated:

(a) Addition of water-soluble derivatives of an acridine or quinoline base, preferably 2-ethoxy-6,9-diaminoacridine-lactate in the pH-range of from 5–10, preferably at about pH 8, up to a final concentration of about 0.8% (weight to volume), the glycoprotein remaining essentially in the supernatant.

(b) Addition of neutral salts until precipitation of the glycoprotein, preferably ammonium sulfate at an about neutral pH-value of from 5–8, up to 30 to 60% of the saturation concentration of ammonium sulfate.

(c) Adsorption of the glycoprotein on a weakly basic ionexchanger such as diethylaminoethyl-cellulose, at a conductivity of the solution of 0–2 mS and neutral or weakly alkaline pH-value (6–9), for example using an about 0.01 M buffer having a pH-value of about 8. A buffer which is preferably used is, for example, tris-hydroxymethylamino-methane-HCl. Elution of the glycoprotein can be effected by lowering the pH-value below pH 7.0 or by increasing the conductivity to more than 5 mS.

(d) Separation on the basis of the size of the molecules (molecular sieve fractionation). Gel-filtration in a column filled with a polymer of a corresponding pore size, for example epichlorohydrin-cross-linked dextran, such as Sephadex ® produced by Messrs. Pharmacia, Uppsala, with the aim of enriching proteins with a molecular weight of about 50,000 is particularly suitable. Products such as Ultrogel ®, produced by Messrs. LKB, Bromma or Bio-Gel ® produced by Bio-Rad Laboratories, Richmond, California, may be likewise used.

(e) Adsorption with hydroxyl-apatite. Since the glycoprotein is not bound by hydroxyl-apatite in dilute phosphate buffer solution, hydroxyl-apatite represents a suitable agent to remove proteins accompanying the glycoprotein from the solution. The protein solution is suitably adjusted to a pH-value around the neutral point and the conductivity of the solution is kept to about 1 mS.

(f) Preparative zone electrophoresis

For carrying out an electrophoresis, a solution which contains the glycoprotein, preferably an alkaline buffer solution, for example a sodium diethylbarbiturate buffer of pH 8.6 and an ionic strength of 0.1, is suitable. The solution is introduced into an apparatus for preparative electrophoresis, for example that described by N. Heimburger and R. Schmidtberger in Behringwerke-Mitteilungen, Volumn 43, pages 83 et seq., in particular on pages 119-120. This carrier electrophoresis apparatus is horizontally arranged in an open trough in which the carrier material is cooled to below 10° C. in order to withdraw the Joule's heat which is generated during the electrophoresis. Polyvinyl chloride or its copolymers in the form of fine granules are preferably used as carrier material substances which are inert toward proteins.

It is recommended to carry out the electrophoresis in the alkaline pH-range, preferably at about pH 8.6, at an ionic strength of 0.08-0.12 and a field strength of 4-6 volts/cm. When using 0.1 M sodium diethylbarbiturate buffer having a pH-value of 8.6, the glycoprotein migrates in the electrical field in the range of the plasmaproteins between $\alpha_1$- and $\alpha_2$-globulins.

For isolating the new glycoprotein, a corresponding zone is cut out and eluted from the inert carrier material with water or aqueous salt solutions, for example 0.5 to 1% sodium chloride solution.

The protein prepared according to the invention has antigenic properties. When immunizing animals with it according to known methods, specific antibodies are formed in the blood of the immunized animals. Their sera can be isolated according to the usual methods and the antibodies contained therein can be enriched. The antisera can be used in known immunological processes for the detection and determination of the new protein in body liquids, in particular in blood serum.

The following Example illustrates the invention.

EXAMPLE 150 kg of deep frozen placentas were comminuted and extracted with 150 l of a 0.5% aqueous sodium chloride solution. The extract was adjusted to pH 8 with 2 N-sodium hydroxide and combined with 50 l of a 3% aqueous solution of diaminoethoxyacridine lactate. After a dwelling time of 1 hour, the supernatant which contained the glycoprotein of the invention (HPG-2) was decanted, combined with 5% solid sodium chloride (11 kg) for separating the diaminoethoxyacridine lactate which still had remained in solution, filtered and combined with 30%—referred to the weight of the liquid—of solid ammonium sulfate and well stirred. After 1 hour the precipitate was filtered off.

500 g of the precipitate deposited on the filter were dissolved in 500 ml of distilled water and dialyzed against a 0.01 molar tris-(oxymethyl)-aminomethane-HCl buffer solution of a pH-value of 7.0 and which contained 0.05% sodium azide. The dialyzed solution was centrifuged and the supernatant was filled up with the same buffer solution to a volume of 2000 ml, adjusted to pH 8.0 with 0.1 N sodium hydroxide solution and stirred with 500 g of wet diethylaminoethyl cellulose (Messrs. SERVA, Heidelberg) for 1 hour.

The diethylaminoethyl cellulose was then separated from the solution by filtration, washed twice with 1 liter portions of 0.01 molar tris-(oxymethyl)-aminomethane-HCl buffer having a pH-value of 8.0 and eluted three times with 500 ml of 0.02 molar tris-(oxymethyl)-aminomethane-HCl buffer, pH 6.5, which contained 0.85% of sodium chloride and 0.05% of sodium azide.

The combined eluates were combined with 30% of ammonium sulfate, referred to the weight of the liquid, and the whole was stirred. The precipitate, which contained the glycoprotein (HPG-2), was dissolved in 300 ml of distilled water. The protein solution was dialyzed against trishydroxymethyl-aminomethane-HCl buffer of pH 8.0 which contained 1.0 mole of sodium chloride/liter and introduced into a column (100×20 cm) filled with Sephadex G-150 and eluted with the mentioned buffer. During the elution, a fractionation of the proteins according to their molecular size took place.

The eluates were subsequently tested with specific antiserum, the fractions containing the glycoprotein (HPG-2) were collected and the proteins were precipitated therefrom as described above with 30% of solid ammonium sulfate.

For further purification, the precipitate was dissolved in 50 ml of water, dialyzed against a 0.005 M phosphate buffer, pH 6.8, and introduced into a column filled with hydroxylapatite (size of the column 3×23 cm). Development of the column was effected with the 0.005 M phosphate buffer, pH 6.8. The glycoprotein (HPG-2) appeared in the eluate. The eluate itself was concentrated on an ultrafilter. The concentrate was then dialyzed against a 0.01 M tris-HCl-buffer, pH 7.0 and adsorbed on DEAE-Sephadex (column 3×23 cm). For eluting and separating the adsorbed proteins, a NaCl-gradient of 0-2% was used. The eluate fractions which contained the glycoprotein (HPG-2) were collected and subsequently concentrated.

For further purification, the concentrated eluate was adsorbed in a 0.075 M ammonium bicarbonate solution and subjected to a preparative zone electrophoresis. The HPG-2 containing zone obtained upon separation was cut out and eluted with physiological salt solution; the eluates were subsequently concentrated on an ultrafilter.

The $\alpha_1$B-glycoprotein which was still present as an impurity was removed by using an adequate immunoadsorbant. For the preparation of the immuno-adsorbant, antibodies directed against $\alpha_1$B-glycoprotein were covalently bound to Sepharose and the resulting absorbant was contacted with the eluate in batchwise operation or in a column. In this process, $\alpha_1$B-glycoprotein was absorbed onto the carrier-bound antibodies, whereas the glycoprotein HPG-2 remained in solution. The solution, which only contained HPG-2, was dialyzed against water and lyophilized. About 10 to 30 mg of the new glycoprotein HPG-2 were obtained.

It showed the following amino-acid composition [frequency with variation coefficient (VC) in %]:

|  | Frequency in Mole % | VC % |
| --- | --- | --- |
| Lysine | 4.41 | 6.92 |
| Histidine | 1.22 | 22.79 |
| Arginine | 1.34 | 9.18 |
| Aspartic | 8.23 | 2.56 |
| Threonine | 6.74 | 2.42 |
| Serine | 5.26 | 6.85 |
| Clutamic acid | 12.59 | 0.49 |
| Proline | 11.27 | 9.20 |
| Glycine | 5.63 | 9.84 |
| Alanine | 15.05 | 6.35 |
| Cystine/2 | 3.65 | 22.76 |
| Valine | 9.89 | 7.94 |
| Methionine | 0.0 | 0.0 |
| Isoleucine | 0.88 | 7.39 |
| Leucine | 9.09 | 3.74 |
| Tyrosine | 1.02 | 30.77 |
| Phenylalanine | 3.60 | 5.14 |
| Tryptophan | 0.14 | 96.98 |

What is claimed is:

1. An isolated, enriched glycoprotein obtainable by fractionating human blood serum or an aqueous extract of human placenta, said glycoprotein having:
    (a) a protein content of 75±6%;
    (b) a carbohydrate content of 24.6±5.2%, consisting of 8.9±2% of hexoses, 7.1±1.5% of N-acetylated hexoseamine, 0.2±0.2% of fucose, and 8.4±1.5% of N-acetylated neuraminic acid;
    (c) a sedimentation coefficient $S_{20w}$ of 2.5±0.3 S;
    (d) a molecular weight of 35,000±5,000, determined in the ultracentrifuge;
    (e) an iso-electric point of pH 3.4±0.4;
    (f) an extinction coefficient $E_1\ _{cm}^{1\%}$ (280 nm) of 1.9±0.3;
    (g) an electrophoretic mobility in the range between the $\alpha_1$- and $\alpha_2$-globulins:
    (h) a specific immunologic reaction with an antibody directed specifically against the glycoprotein.

2. A glycoprotein as in claim 1 wherein said protein solution is an extract of human placenta.

3. An antiserum against the glycoprotein of claim 1.